United States Patent [19]

Sitnik

[11] Patent Number: 5,055,102
[45] Date of Patent: Oct. 8, 1991

[54] SWING-AWAY DISPOSABLE SYRINGE NEEDLE COVER

[76] Inventor: Lee Sitnik, 209 Glenridge Ct., Columbia, S.C. 29212

[21] Appl. No.: 534,506

[22] Filed: Jun. 4, 1990

[51] Int. Cl.⁵ .............................................. A61M 5/32
[52] U.S. Cl. .................................... 604/192; 604/263
[58] Field of Search ................ 604/192, 263, 187, 198

[56] References Cited

U.S. PATENT DOCUMENTS

| | | |
|---|---|---|
| 4,664,654 | 5/1987 | Strauss . |
| 4,863,435 | 9/1989 | Sturman . |
| 4,880,413 | 11/1989 | Giuffre . |
| 4,886,503 | 12/1989 | Miller ............................ 604/198 X |
| 4,900,309 | 2/1990 | Netherton . |
| 4,944,397 | 7/1990 | Miller .................................. 604/192 |

FOREIGN PATENT DOCUMENTS 2618685  2/1989  France ................................ 604/263

*Primary Examiner*—John D. Yasko
*Attorney, Agent, or Firm*—F. Rhett Brockington

[57] ABSTRACT

A needle cover for a needle on a syringe which can be removed through the application of a single finger force against a lever arm that is integral with the needle cover, where said force causes the needle cover to rotate laterally away from the needle sheathed within, wherein the continued application of finger force deflects the needle over from a coaxial position, therein exposing the sheathed needle, to a perpendicular position where the needle cover is well out of the way of subsequent activity, where said needle cover is comprised of a tapered tube of sufficient length and diameter to sheath the needle and the hub, and extending lengthwise is a longitudianl slit which expands to an elongated hole in a wall of the tapered tube, and opposite to the elongated hole is a partially open hole that opens toward the syringe, where these two holes create a space into which the hub can move when the tube is rotated, where the partial opening serves as a constriction which prevents the needle cover from rotating unless forced. Opposing perforations in the wall of the tapered tube enable the tube to pivot at the hub, which has radially extending axial elements. The needle cover can be locked into the sheathed coaxial position by pushing tapered tube down against the syringe.

4 Claims, 6 Drawing Sheets

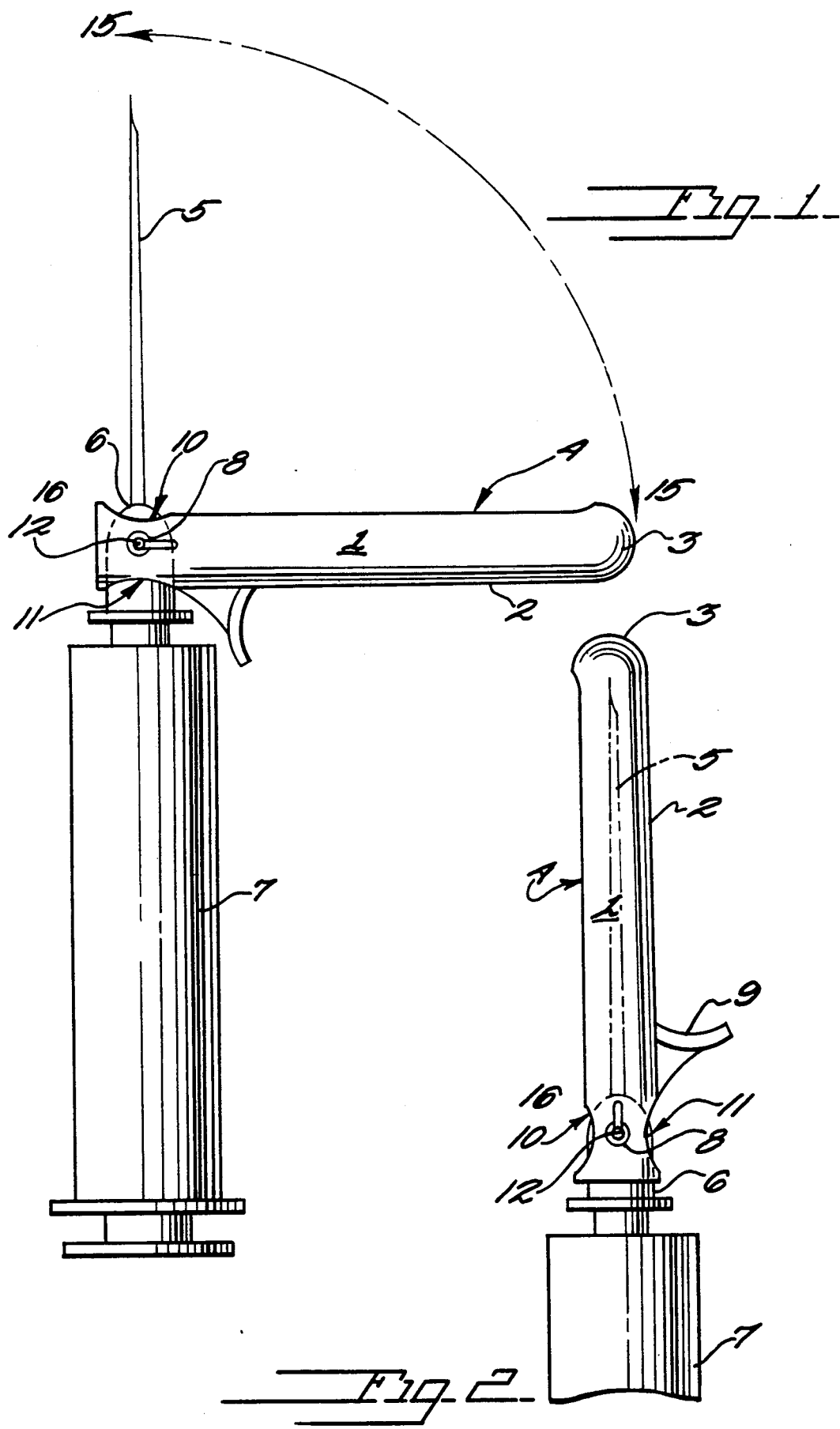

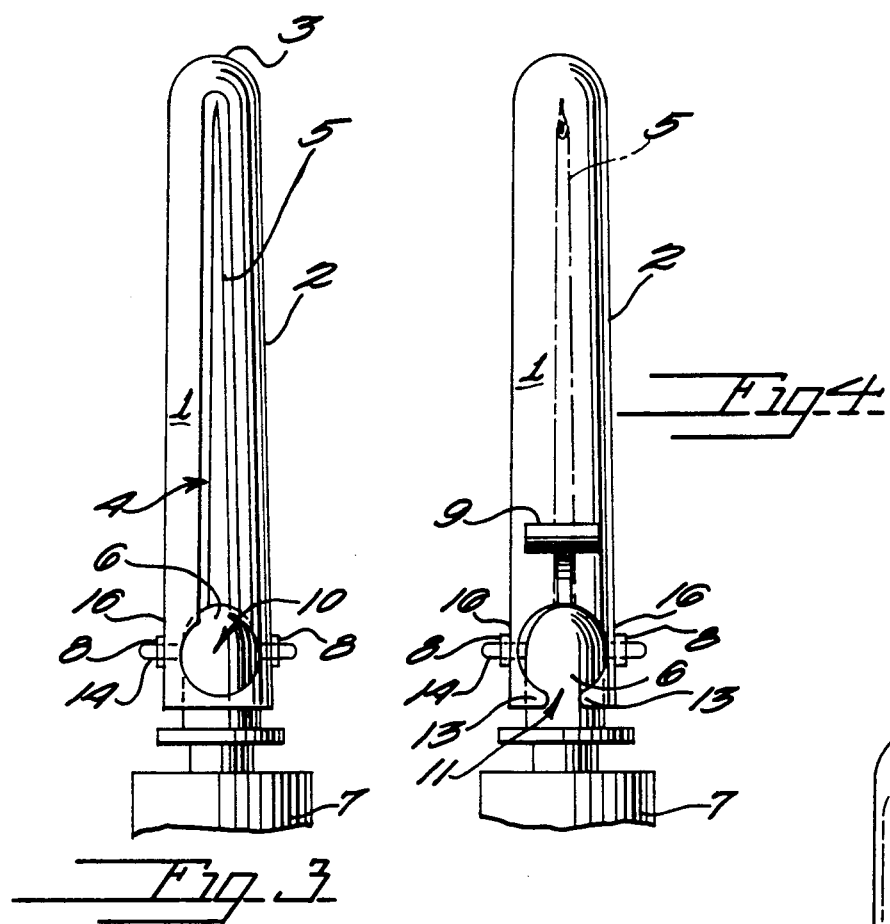
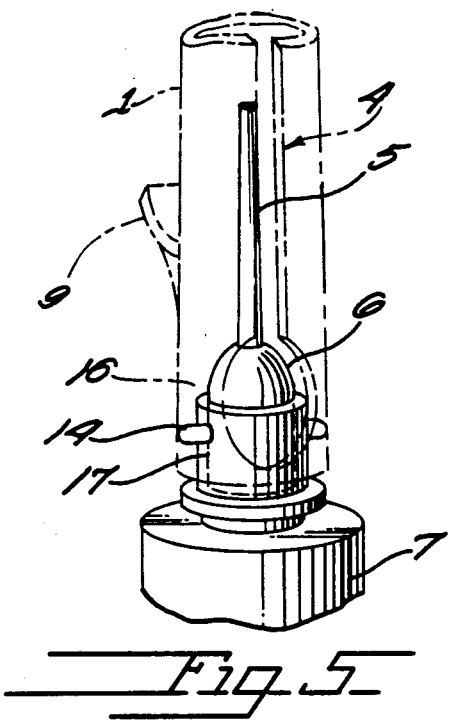
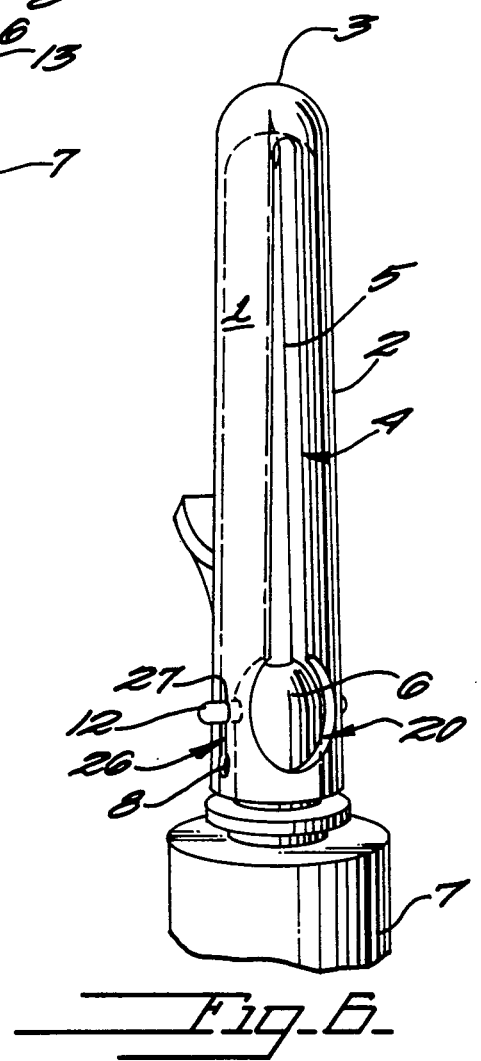

SWING-AWAY DISPOSABLE SYRINGE NEEDLE COVER

BACKGROUND AND SUMMARY OF THE INVENTION

The present invention relates generally to needle covers, and more specifically to disposable hypodermic needle covers designed to minimize accidental needle sticks and enhance ease of use.

In using a disposable syringe, particularly one fitted with a hypodermic needle, the syringe is removed from a sterile package, the conventional needle cover is grasped and removed using one hand to hold the syringe and another to hold the cover, the needle is inserted into the serum bottle, the bottle is inverted and the piston of the syringe is pushed inward, therein forcing air into the bottle. With the bottle inverted the syringe is filled by retracting the piston until the desired quantity of serum has been drawn into the barrel of the syringe. The syringe is then recapped, using the previously removed needle cover, and positioned on a tray for conveyance to the patient's room. Prior to the actual injection the syringe has to be uncapped again, and then, following the injection, it is recapped, for the third time, prior to disposal. Typically, the spent syringe is disposed of in a dedicated disposal box, which is designed to prevent the syringe from being utilized again, by authorized or unauthorized personnel. The outlined procedure for using a syringe creates a significant number of opportunities for the administering medical personnel to accidentally stick themselves with the needle. The syringe disposal box can be particularly onerous as it can be a source of multiple uncapped needles. Once a shot has been administered there is much less perceived necessity for diligently recapping the needle. Not infrequently, the syringe is not recapped prior to disposal, and someone, subsequently discarding a spent syringe in the syringe disposal box, has an excellent chance of accidentally sticking themselves.

Sturman in his U.S. Pat. No. 4,863,435 cites a report by Biomedical Business International that estimates that there are more than 800,000 accidental needle sticks each year. Sturman discloses a safety hypodermic syringe, wherein following the injection, the tip of the needle is covered by releasing a spring fitted with a cap.

Netherton's U.S. Pat. No. 4,900,309 discloses an alternate solution to preventing needle sticks. In his invention, the entrance of the needle cover is fitted with a flange, wherein the flange serves as a shield.

Other related prior art includes Giuffre's U.S. Pat. No. 4,880,413 funnel shaped needle cover, and Strauss U.S. Pat. No. 4,664,654 which discloses an "Automatic Protracting and Locking Hypodermic Needle Guard", that has a sliding member that can be locked in place to protect the point of the needle.

The instant invention is a needle cover for a disposable hypodermic needle mounted on a syringe, wherein the cover can be removed and repositioned with one hand without ever having to come near the point of the needle. The swing-away needle cover is removed using one finger by pulling down a lever arm attached to the cover, which causes the cover to rotate away, therein exposing the needle. The cover is repositioned by reversing the process. The cover, during procedures requiring exposure of the needle such as filling or injecting, is rotated approximately perpendicular to the axis of the needle, well out of the way of the on going activity. The needle cover snaps into place in the coaxial and in the perpendicular positions. The swing-away needle cover, at first glance, appears to be substantially like a conventional needle cover. It is comprised of a resilient plastic like polyethylene or polypropylene and presents a relatively narrow profile like a conventional needle cover, unencumbered by large shields or mechanically complex attachments. The swing-away needle cover rotates away from the needle, where the needle hub is the pivot point of rotation. The cover is substantially a tapered tube with a longitudinal slit, the slit being sufficiently long and wide to permit the free passage of the needle through the slit. The tapered tube serves as a protecting sleeve covering and sheathing the longitudinal length of the needle, wherein the attenuated end of the tapered tube, covering the tip of the needle, is sealed with a closing cap. At the other end of the tapered tube, covering the hub of the needle, the longitudinal slit widens to an longitudinally elongated hole having a narrow radius of sufficient width to permit the needle end of the hub to fit through, with little or no distortion of the hole. The opposing side of the tapered tube has a partially open hole, wherein the entrance to the hole is constricted by a pair of tabs. Once past the tabs the radius is sufficiently wide to permit the syringe end of the hub to fit through. The constricting tabs prevent the needle cover from rotating unless sufficient force, applied against the lever arm, is supplied to distort the tabs wide enough to let the hub pass through. The partially open hole faces toward the syringe. The tapered tube has a pair of bearings located in the wall of the tube adjacent to the hub. The bearings, which can be little more than perforations in the wall, have an axis which is perpendicular to the plane of rotation of the needle cover. The bearings are attached to the hub through a hinging member that is substantially a pair of axial elements emanating radially from the hub or a sleeve on the hub hinged perpendicular to the longitudinal slit. The hinging member enables the needle cover to rotate away from the tip of the needle, in a plane defined by the longitudinal slit and the needle. When the tapered tube is forced to rotate from the coaxial position toward the perpendicular position, the tabs of the partial opening initially resists the deflection, and only when adequate force has been applied to cause the hub to press open the tabs does the tapered tube move away from the coaxial position. As the angle of deflection from the coaxial position increases the needle emerges from the longitudinal slit, and the needle end of the hub moves into the elongated hole which is contiguous with the longitudinal slit, and the syringe end of the hub moves past the tabs and into the central portion of the partially open hole. The tabs act as a kind of safe guard lock, preventing the needle cover from moving either into or out of the coaxial or perpendicular positions unless forced by pressure on the lever arm. The tapered tube is fitted with an upwardly curved lever arm on the side opposite the longitudinal slit. The lever arm is distal to the needle end of the hub, when the cover is in the coaxial position. The lever arm is constructed so as to be of sufficient length and strength as to enable the user of the syringe to pull the tapered tube out of the coaxial position and into the perpendicular position, and vice versa.

BRIEF DESCRIPTION OF THE DRAWINGS

FIG. 1 is a side view of the swing-away disposable needle cover on a syringe fitted with a hypodermic needle with the cover moved to the perpendicular position. The needle cover is fabricated using a transparent material.

FIG. 2 is a side view of the swing-away disposable needle cover shown in FIG. 1 with the cover in the coaxial position. The needle is sheathed.

FIG. 3 is a perspective view of the needle cover shown in FIG. 2 as seen from observation point 3—3, which illustrates the longitudinal slit and elongated hole.

FIG. 4 is a perspective view of the needle cover shown in FIG. 2 as seen from observation point 4—4, which illustrates the partially open hole into which the hub rotates.

FIG. 5 is a perspective view of an alternate embodiment of the swing-away disposable syringe needle cover wherein the hinging member is comprised of a sleeve which fits on the hub and from which project the axial elements.

FIG. 6 is an enlarged perspective drawing of a preferred embodiment of the swing-away disposable needle cover, wherein the cover has been slid down on the hub, which consequently makes rotation around the hub very difficult, and also raises the tip of the needle upward into the protective closing cap, which takes the needle out of alignment with the longitudinal slit.

DETAILED DESCRIPTION OF THE PREFERRED EMBODIMENT

Referring now in detail to the drawings and, in particular to FIGS. 1 and 2 thereof, the needle cover 1 is shown on a syringe 7 fitted with a hypodermic needle 5. In FIG. 1 the needle cover 1 is in the unsheathed or perpendicular position, and in FIG. 2 the needle is sheathed within the needle cover and this is the coaxial position. The needle cover 1 is comprises of a tapered tube 2 which extends over the needle 5 and the hub 6. The hub 6 mounts the needle to the syringe 7. The tapered tube 2 has a longitudinal slit 4 that extends the length of the needle, where the slit 4 is of sufficient size that the needle cover can be removed laterally. Additionally, the walls of the tapered tube 2 have been cut away in the region adjacent to the hub, such that the walls of the tube do not prevent rotation around the hub. Referring to FIG. 3, which is a perspective view of the needle cover 1 taken from observation point 3—3, one can gain a better understanding of just how the tapered tube 2 is constructed. The longitudinal slit 4 expands into an elongated hole 10 through which the hub 6 projects when the needle cover is rotated to the perpendicular position. A view of the needle cover 1 as seen from the opposing side, observation point 4—4, is shown in FIG. 4. The entrance to the partially open hole 11 is constricted with tabs 13, which prevent the needle cover from rotating unless sufficient force is applied against the lever arm 9 to push the tabs 13 out of the way. The tabs 13 serve as a kind of locking mechanism in both the coaxial and the perpendicular positions. In FIGS. 3-4 the needle cover 1 is shown pivoting on a hinging member which consists of axial elements 14 which project radially from the hub perpendicular to the plane of rotation, line 15—15 shown in FIG. 1. The needle cover 1 pivots on bearings 8, which are located laterally at opposing positions in the wall of the tapered tube 2. These bearings 8 are substantially just perforations in the wall, through which project the axial elements 14. Each bearing 8 has a longitudinal groove 16, into which the axial elements can shoved, if the tapered tube 2 is forced down against the syringe 7. This action displaces the hub from the elongated hole 10 and the partially open hole 11, therein precluding any further rotation from the coaxial position. Typically, after the syringe is spent, then the needle cover would be returned to the coaxial position using the lever arm 9, and then the needle cover would be pushed down on the syringe therein locking the cover. The syringe could be disposed with the knowledge that there was minimal chance of the needle becoming exposed.

In a second preferred embodiment, the hinging member consists of a sleeve 17, shown in FIG. 5, which slides over the hub 6. The sleeve 17 is secured to the hub. Axial elements 14 project from the sleeve 17, instead of the hub 6 itself.

In a third preferred embodiment, shown in FIG. 6, the needle cover 1 pivots on bearings 8, which are located laterally at opposing positions in the wall of the tapered tube 2. Each bearing 8 has a vertical slit 26, which terminates in a locking hole 27 into which an axial element will move to, when the tapered tube 2 is forced down against the syringe 7. This action forces the needle up into the cover, such that the tip of the needle is lodged in the closing cap 3. In this embodiment the axial elements 14 snap into the locking holes 27 after they are pushed through the vertical slit 26, the snapping action serving to prevent the needle cover from accidently sliding upward and opening during or following disposal. In this embodiment, to facilate easier distortion of the tapered tube 2, particularly when it is locked down for disposal, the elongated hole 10, seen in the first embodiment, is replaced with a slit elongated hole 20. The slit elongated hole 20 is easier to bend. Typically, after the syringe is spent, then the needle cover would be returned to the coaxial position using the lever arm 9, and then the needle cover would be pushed down on the syringe therein locking the cover in the locking holes 27.

I claim:

1. A needle cover for a needle on a syringe where said needle cover, which hingedly pivots on axial elements radial to a needle hub, can be removed through the application of a single finger force against a lever arm that is integral with the needle cover, where said force causes the needle cover to rotate laterally away from the needle sheathed within, wherein the continued application of finger force deflects the needle cover from a coaxial position, therein exposing the sheathed needle, to a perpendicular position where the needle cover is well out of the way of subsequent activity, where said needle cover prior to disposal can be locked into a non-rotatable position, by returning the needle cover to the coaxial position and shoving the needle cover down onto the axial elements radial to the needle hub, where said needle cover is comprised of:

a tube of sufficient length and diameter to sheath the needle and the needle hub, wherein the tube is closed on one end, and has, extending lengthwise from the closed end, a longitudinal slit, which is sufficiently long and wide to permit the needle to traverse through the slit laterally, wherein said longitudinal slit, in an area adjacent to the needle hub, expands to an elongated hole, where the elongated hole is of sufficient size as to accommodate the needle hub when the needle cover is rotated to the perpendicular position, and in an opposing arc of the tube, essentially opposite to the elongated hole is a partially open hole that opens toward the syringe, wherein the partially open hole is of sufficient size as to accommodate the needle hub when the needle cover is rotated to the perpendicular position, and where said tube has a lever arm, which projects outward from the tube, wherein said lever arm is constructed so as to be of sufficient length and strength as to enable a user of the syringe to move the tube out of the coaxial position and into the perpendicular position, and the tube has bearings that are axially perpendicular to the longitudinal slit and positioned such that the bearings are aligned with said axial elements radial to the needle hub, and wherein said bearings have a longitudinal groove, such that when the tube is forced down, the bearings distort against the pressure of the axial elements and the tube is displaced past the axial elements into to the longitudinal groove therein locking the needle cover in the coaxial position.

2. A needle cover as claimed in claim 1 wherein the needle cover is fabricated using a resilient polymer, and the preferred resilient polymer is polyethylene.

3. A needle cover as claimed in claim 2 where the bearing is comprised of a circular perforation in a wall of the tube.

4. A needle cover as claimed in claim 1 wherein the partially open hole that opens toward the syringe has a pair of tabs, located proximal to the syringe, which constrict passage of the needle hub into the partially open hole when the needle cover is deflected from its coaxial position, until sufficient force is applied to cause the tabs to distort enabling the needle hub to push through the constriction into the partially open hole, and that said constriction serves to hold the needle cover in the coaxial position, and alternatively, that said pair of tabs tend to hold the needle cover in the perpendicular position once the needle hub is within the partially open hole.

* * * * *